United States Patent
Bailey et al.

(10) Patent No.: US 11,700,939 B2
(45) Date of Patent: Jul. 18, 2023

(54) CUSTOMIZABLE CABINET

(71) Applicant: Bailey Hill, LLC

(72) Inventors: John Taylor Bailey, Longview, TX (US); Kersten John Braden Hill, Longview, TX (US); Teddy Charles Stevens, Longview, TX (US); Michael Shane Whitehurst, Longview, TX (US)

( * ) Notice: Subject to any disclaimer, the term of this patent is extended or adjusted under 35 U.S.C. 154(b) by 2 days.

(21) Appl. No.: 17/403,446

(22) Filed: Aug. 16, 2021

(65) Prior Publication Data

US 2022/0047072 A1 Feb. 17, 2022

Related U.S. Application Data

(60) Provisional application No. 63/066,054, filed on Aug. 14, 2020.

(51) Int. Cl.
| | | |
|---|---|---|
| *A47B 67/02* | (2006.01) | |
| *A47B 57/00* | (2006.01) | |
| *A61B 42/40* | (2016.01) | |
| *A47B 57/10* | (2006.01) | |
| *A61B 50/10* | (2016.01) | |

(52) U.S. Cl.
CPC .............. *A47B 57/00* (2013.01); *A47B 57/10* (2013.01); *A47B 67/02* (2013.01); *A61B 42/40* (2016.02); *A61B 2050/105* (2016.02)

(58) Field of Classification Search
CPC ......... A47B 57/00; A47B 57/10; A47B 67/02; A61B 42/40; A61B 2050/105
See application file for complete search history.

(56) References Cited

U.S. PATENT DOCUMENTS

| | | | | |
|---|---|---|---|---|
| 4,094,416 A | * | 6/1978 | Smith | A47B 45/00 D6/520 |
| 5,139,322 A | * | 8/1992 | Aisley | E05F 1/066 312/351 |
| 5,143,229 A | * | 9/1992 | LaCorte | B65H 35/002 211/85.28 |
| 5,143,230 A | * | 9/1992 | LaCorte | B65H 35/002 D6/520 |
| 5,647,651 A | * | 7/1997 | Kim | A47B 67/00 312/291 |
| 6,820,753 B2 | * | 11/2004 | Kurtz | A47K 10/20 211/49.1 |

(Continued)

FOREIGN PATENT DOCUMENTS

| | | | | |
|---|---|---|---|---|
| DE | 102005029379 A1 | * | 2/2007 | A61B 42/40 |
| GB | 2510428 A | * | 8/2014 | A61B 42/40 |
| GB | 2528242 A | * | 1/2016 | A61B 42/40 |

*Primary Examiner* — Kimberley S Wright

(74) *Attorney, Agent, or Firm* — Bobby W. Braxton; Gregory Perrrone; Braxton Perrone, PLLC

(57) ABSTRACT

A system and method for a cabinet. The cabinet has at least two mounts. The cabinet further has at least two covers. The covers are releasably couple to the mounts. When the covers are coupled there is an opening between adjacent covers which houses an item which can be retrieved through the opening. The covers can have tabs which couple with slots in the mounts. The result is an interchangeable cabinet which allows the user to change the contents being housed by moving the covers and adjusting the size of the opening to account for larger or smaller contents.

19 Claims, 6 Drawing Sheets

(56) References Cited

U.S. PATENT DOCUMENTS

| | | | | |
|---|---|---|---|---|
| 6,955,268 B2* | 10/2005 | Waldron | ............ | G11B 33/0466 |
| | | | | 211/59.3 |
| 7,246,710 B2* | 7/2007 | Graneto, III | ........... | A61G 12/00 |
| | | | | 211/90.01 |
| 7,762,635 B2* | 7/2010 | Spoljaric | ................. | A61F 17/00 |
| | | | | 312/291 |
| 9,307,837 B2* | 4/2016 | Wood | ...................... | A47B 67/02 |
| 10,352,092 B2* | 7/2019 | DeGraaf | ................. | E06B 5/006 |
| 10,787,307 B2* | 9/2020 | Modha | .................... | B65D 5/542 |
| 10,794,111 B2* | 10/2020 | DeGraaf | ................ | A47B 67/00 |
| 2004/0099623 A1* | 5/2004 | Kurtz | ..................... | A47K 10/20 |
| | | | | 248/905 |
| 2008/0111454 A1* | 5/2008 | Spoljaric | ................ | A47B 67/02 |
| | | | | 312/209 |
| 2011/0155870 A1* | 6/2011 | Tyner | ..................... | A61B 50/10 |
| | | | | 248/298.1 |
| 2011/0192861 A1* | 8/2011 | Bates | ..................... | A61B 42/40 |
| | | | | 221/124 |
| 2011/0279001 A1* | 11/2011 | Peters | ................... | A47B 67/00 |
| | | | | 312/209 |
| 2012/0068027 A1* | 3/2012 | Tyner | ........................ | A47F 1/04 |
| | | | | 248/298.1 |
| 2015/0320238 A1* | 11/2015 | DeGraaf | ................... | A47F 3/06 |
| | | | | 312/138.1 |
| 2015/0374121 A1* | 12/2015 | Wood | ..................... | A47B 96/04 |
| | | | | 312/245 |
| 2019/0338584 A1* | 11/2019 | DeGraaf | .................... | A47F 3/06 |
| 2021/0171272 A1* | 6/2021 | Olschan | ................. | A61F 17/00 |

* cited by examiner

CUSTOMIZABLE CABINET

PRIORITY

The present application claims benefit of U.S. Provisional Application No. 63/066,054 filed Aug. 14, 2020, all of which are hereby incorporated herein by reference in their entirety and made part of the present application.

BACKGROUND OF THE INVENTION

Technical Field

The present invention relates to a system and method for customizable cabinet.

Description of Related Art

Cabinets are often manufactured with a set or specified configuration. However, the needs of the end users can vary and can change over time. Consequently, there is a need for a customizable and adjustable cabinet.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

DETAILED DESCRIPTION

Several embodiments of Applicant's invention will now be described with reference to the drawings. Unless otherwise noted, like elements will be identified by identical numbers throughout all figures. The invention illustratively disclosed herein suitably may be practiced in the absence of any element which is not specifically disclosed herein.

Cabinets are used for a variety of purposes. They house and organize items. They can be used in residential, commercial, industrial, and medical facilities. Cabinets can be affixed to any structure such as a wall or door. Additionally, cabinets can be stand-alone objects which do not nee the support of an external structure such as a wall.

Cabinets are offered in a specific configuration. Often, these configurations were static and not adjustable. Consequently, when a customer ordered a cabinet, they were set with that configuration for the life of the cabinet. If they wanted a new configuration, that would require a new configuration. In one embodiment, an adjustable and customizable cabinet is disclosed. This allows the user to modify the cabinet based on their current needs.

One embodiment will be discussed in reference to a medical cabinet which houses and dispenses Personal Protection Equipment ("PPE"). As discussed in more detail, however, this is for illustrative purposes only and should not be deemed limiting. The cabinets can be used in a wide variety of applications and house a wide variety of items.

Figure 1:
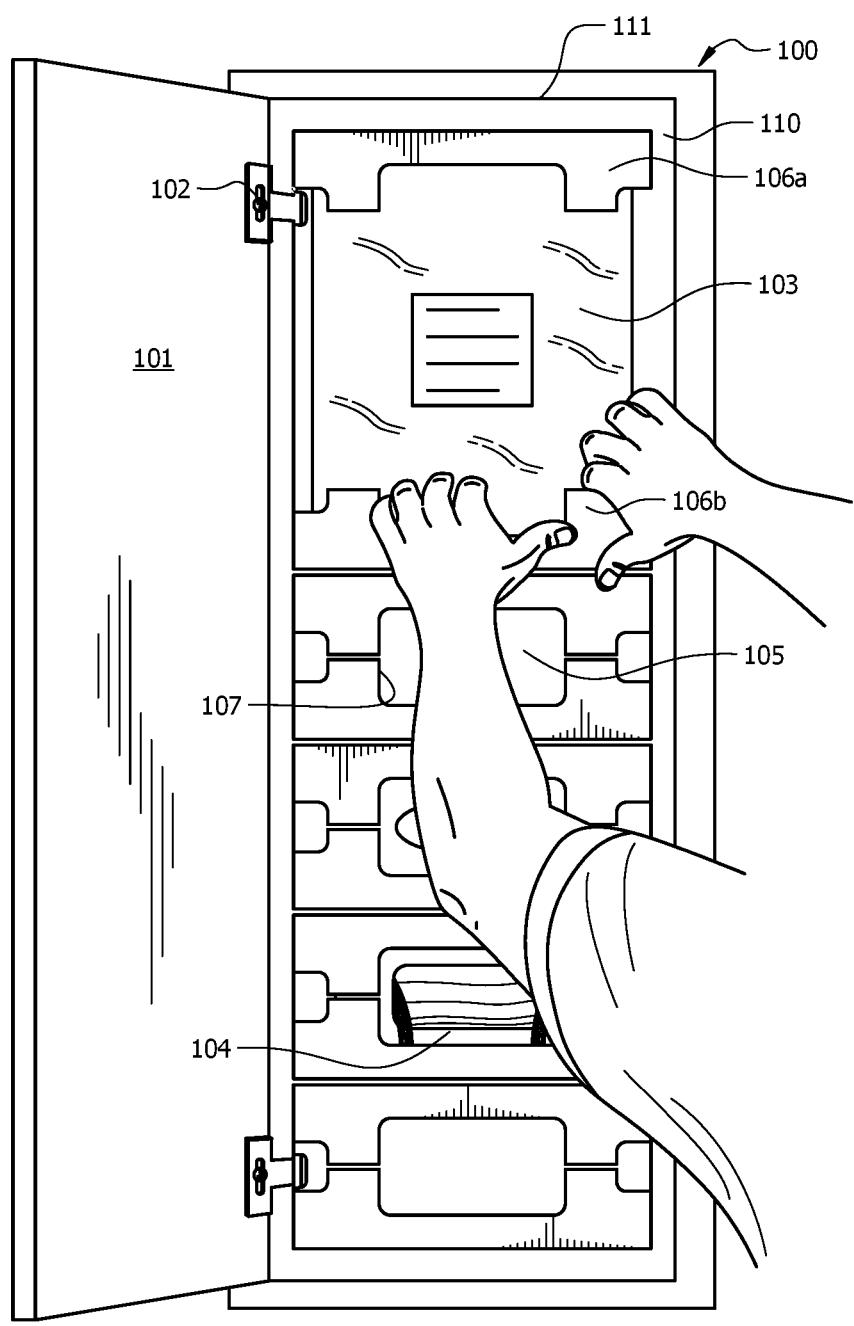
FIG. 1 is a perspective view of a cabinet in one embodiment.

FIG. 1 is a perspective view of a cabinet in one embodiment. As shown the cabinet comprises a door 101 which couples to the cabinet 100 via a hinge 102. The door 101 can comprise virtually any material. In one embodiment the cabinet 100 is coupled via a releaseable hinge 102 such that the door 101 can be removed. In other embodiments, a door 101 is not utilized.

In one embodiment the cabinet 100 has an outer shell 111. This can comprise any material including wood, plastic, metal, and combinations thereof. The outer shell 111 is what users see on the outside of the cabinet 100.

In one embodiment adjacent and inside of the outer shell 111 is a mount 110. The mounts 110, as depicted, are vertical couplers which are attached to the cabinet 100 and which covers 106, and shelves 109 can attach, as discussed in more detail below. Thus, in one embodiment the system comprises at least two mounts. As shown the mounts 110 are parallel to one another.

As shown in FIG. 1, there are a first item 103 and a second item 104. As shown, the first and second items 103, 104 comprise a different size. The contents/items are accessible through an opening 105 from which the items can be retrieved. The opening 105 is created by opposing covers 106.

The opening 105, in one embodiment, is a void or absence of material. In this way, there is a window or slot through which the interior items are visible and through which they may be retrieved. As depicted, the first item 103 comprises aprons whereas the second items 104 comprises gloves. In still other embodiments the first or second items can comprise gloves, masks, beard coverings, etc. While a first and second items are discussed, in other embodiments there will be more than two separate items.

As noted, the covers 106 create the opening 105. As shown there is a top cover 106a and a bottom cover 106b. These two together create an opening. Thus, in one embodiment adjacent covers 106 create an opening in the space between the covers 106. The size of the opening 105 can also be controlled by modifying the shape of the covers 106. As shown, the covers 106 are U-shaped. Thus, even when covers 106 are placed directly adjacent one another, as shown in the second from the top pair of covers 106 in FIG. 1, there is still an opening 105 due to the U-shape of the covers 106. The covers 106 can have virtually any shape including U-shape, V-shaped, semi-circular, rectangular, etc.

As shown, the opening for the first item 103, the apron, is larger than the opening for the second opening for the gloves 104. This illustrates one benefit of the system discussed herein—the ability to alter the size of the opening by adjusting the distance between covers 106. Thus, even where the covers 106 has the same shape and size, as depicted in FIG. 1, the opening 105 can be adjusted by varying the distance between adjacent covers 106.

While a top 106a and bottom 106b cover has been depicted, this is for illustrative purposes only and should not be deemed limiting. In other embodiments the covers can be on the left and right, for example. Thus, the purpose of the covers 106 is to provide an opening which can be adjusted depending upon the size of the contents. In one embodiment the covers 106 are oriented approximately perpendicular to the mounts 110. Here, the mounts 110 are vertical and the covers 106 are oriented horizontally. If the mounts 110 are horizontally oriented, then the covers 106 will be vertically oriented.

As seen, the cabinet 100 further comprises a back support 107, in one embodiment. The back support 107 provides the outer limit that the contents can be pressed. The back support 107 offers pressure to ensure the glove box, as an example, remains in the outward position. In some embodiments without a back support 107, when a user tries to obtain gloves, the pressure applied by the user can force the glove box backwards into the cabinet 100. The back support 107 prevents this from happening.

The cover 106 can comprise virtually any material. It can include wood, metal, plastic, rubber, and combinations thereof. In one embodiment, the cover 106 comprises antimicrobial, anti-fungal, and/or anti-bacterial properties. In a medical environment this is a benefit as it reduces the spread of germs, viruses, etc. Further, while these properties are addressed with respect to the cover 106, in other embodiments the door 101, outer shell 111, etc. can also exhibit properties which reduce the spread of germs, viruses, etc.

Figure 2:
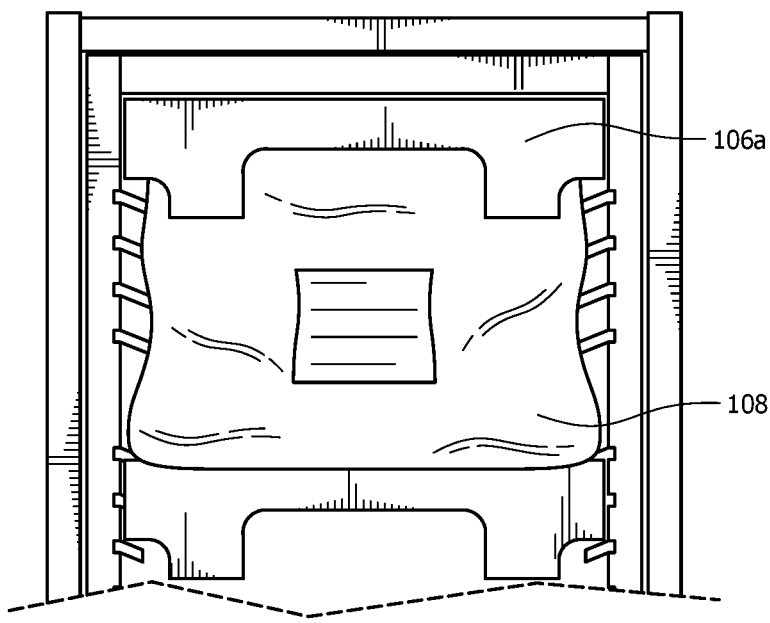
FIG. 2 is a perspective view of a cabinet wherein one cover has been removed.

To help illustrate the system and method discussed herein, a series of figures will be used to demonstrate how the configuration of the cabinet 100 can be changed. FIG. 2 shows an embodiment wherein one cover has been removed. As shown, the door 101 has been removed. In one embodiment this is necessary to be able to access the left mount 110. In other embodiments, however, removing the door 101 is not necessary.

As shown in FIG. 2, the lower cover 106*b* has been removed. As will be discussed in more detail below, in one embodiment the cover 106 couples to the slot 108 in the mount 110. In one embodiment the covers 106 are releasably coupled with the mounts 110. Releasably coupling refers to a coupling which is not permanent and which can be adjusted. In one embodiment the coupling of the cover 106 requires no tools—no screw drivers, no screws, etc. Instead, the shape between the slot 108 and the cover 106 allows the cover 106 to fit via friction.

Figure 3:
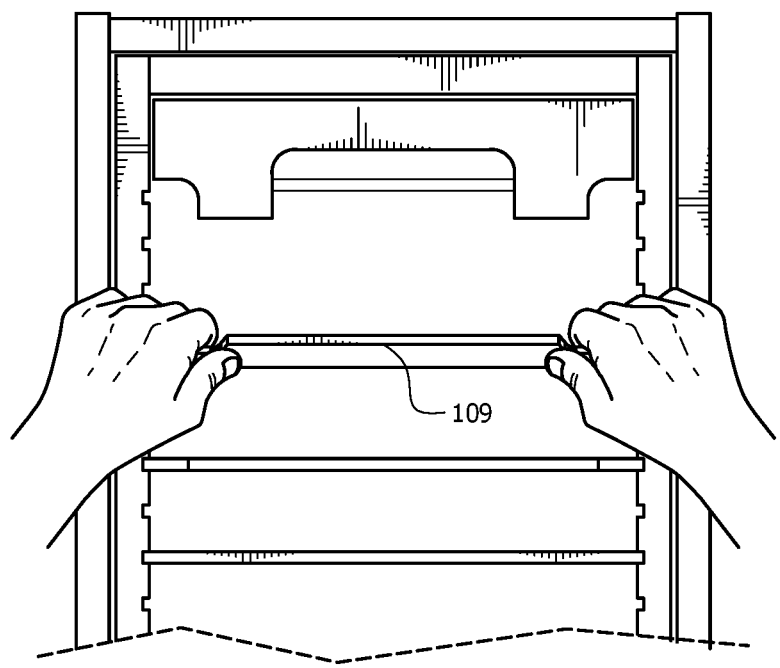
FIG. 3 is a perspective view of a cabinet with the items removed in one embodiment.

After the lower cover 106*b* has been removed, the contents are removed. FIG. 3 is a perspective view of a cabinet with the items removed in one embodiment. As shown, a shelf 109 has been inserted. As noted, in one embodiment the mounts 110 comprise slots 108. The shelf 109 is sized to fit within the left and right slots 108 on the mounts 110. In this embodiment the slots 108 extend horizontally along the mount 110. As with the covers 106, in one embodiment no tools are needed to install or remove the shelf 109. The shelf 109 cuts the previous large single opening into two separate smaller openings.

Figure 4:
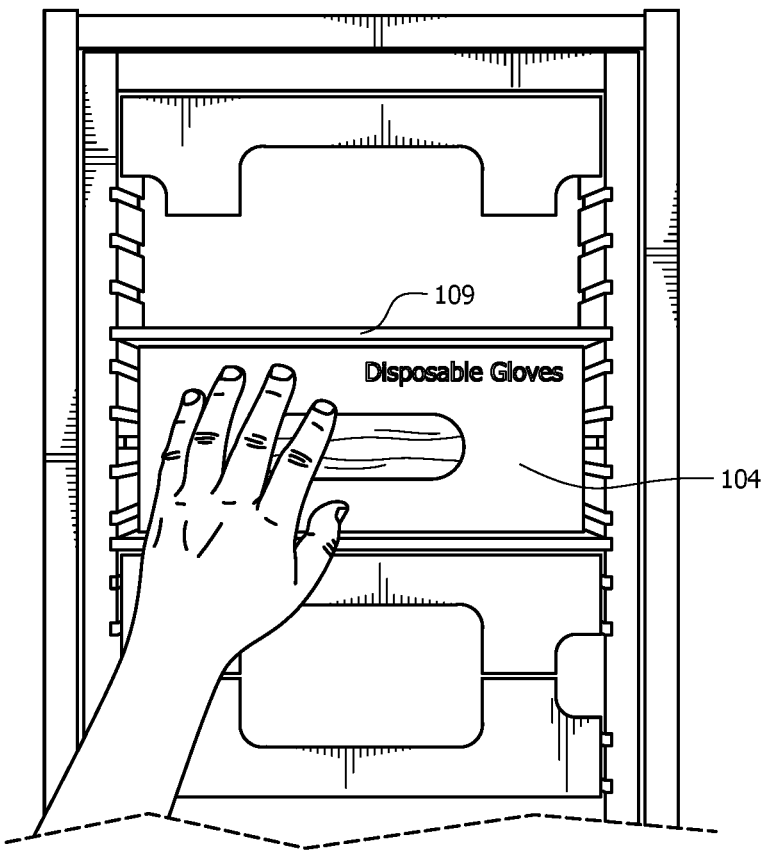
FIG. 4 is a perspective view of items being installed in an opening.

FIG. 4 is a perspective view of items being installed in an opening in one embodiment. As shown, a comparatively smaller contents, in this case a box of gloves, is inserted into the smaller lower opening. Previously these two separate openings were really one single opening housing aprons. This illustrates the versatility of the system. What was once a larger opening for dispensing a large item such as an apron, has been modified to dispense a smaller item such as gloves. This was accomplished without changing the permanent structure of the cabinet. Further, in some embodiments, this is accomplished without any external tools, external screws, etc. This shows that the cabinet can easily and readily be adapted to change the items to be dispensed. If gloves are needed more than aprons, as an example, the covers 106 can be removed and repositioned as necessary to create the desired opening to dispense a smaller item.

Figure 5:
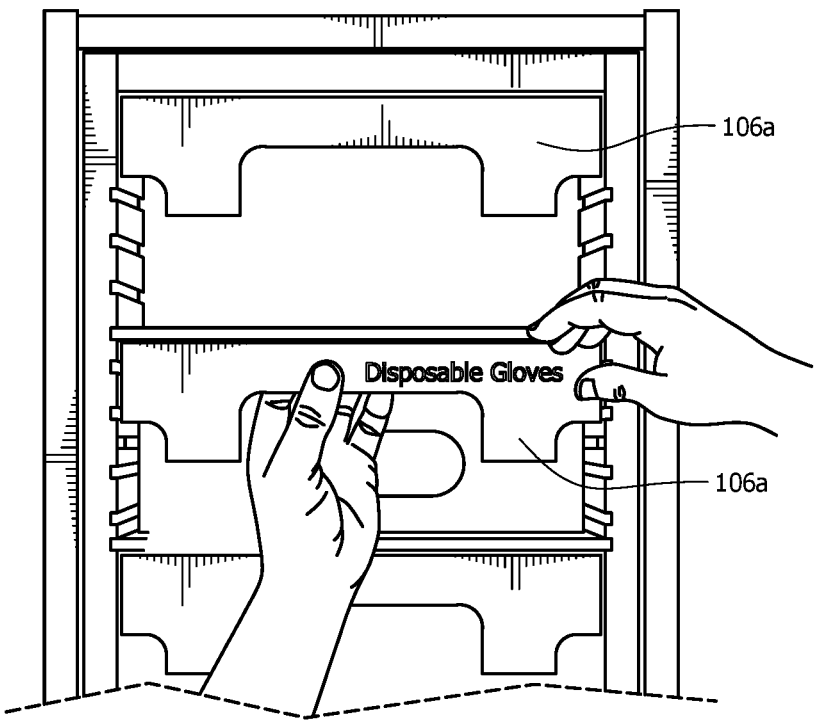
FIG. 5 shows an upper cover being coupled to each mount in one embodiment.

FIG. 5 shows an upper cover being coupled to each mount in one embodiment. FIG. 5 is a continuation of the transformation shown in FIG. 4. The same box of gloves is being covered with an upper mount 106*a*. As shown, the top of the upper cover 106*a* coincides with the location of the shelf 109, which was shown in FIG. 4. The newly installed upper cover 106 delineates the top opening from the lower opening. As noted, in one embodiment the upper cover 106*a* is installed without the need for separate tools, or anchoring devices, etc. Instead, the upper cover 106*a* couples via friction fitting due to the shapes between the cover 106 and the mount 110. The covers 106 create backpressure to prevent the entire glove box from being pulled down when a user retrieves a pair of gloves.

Figure 6:
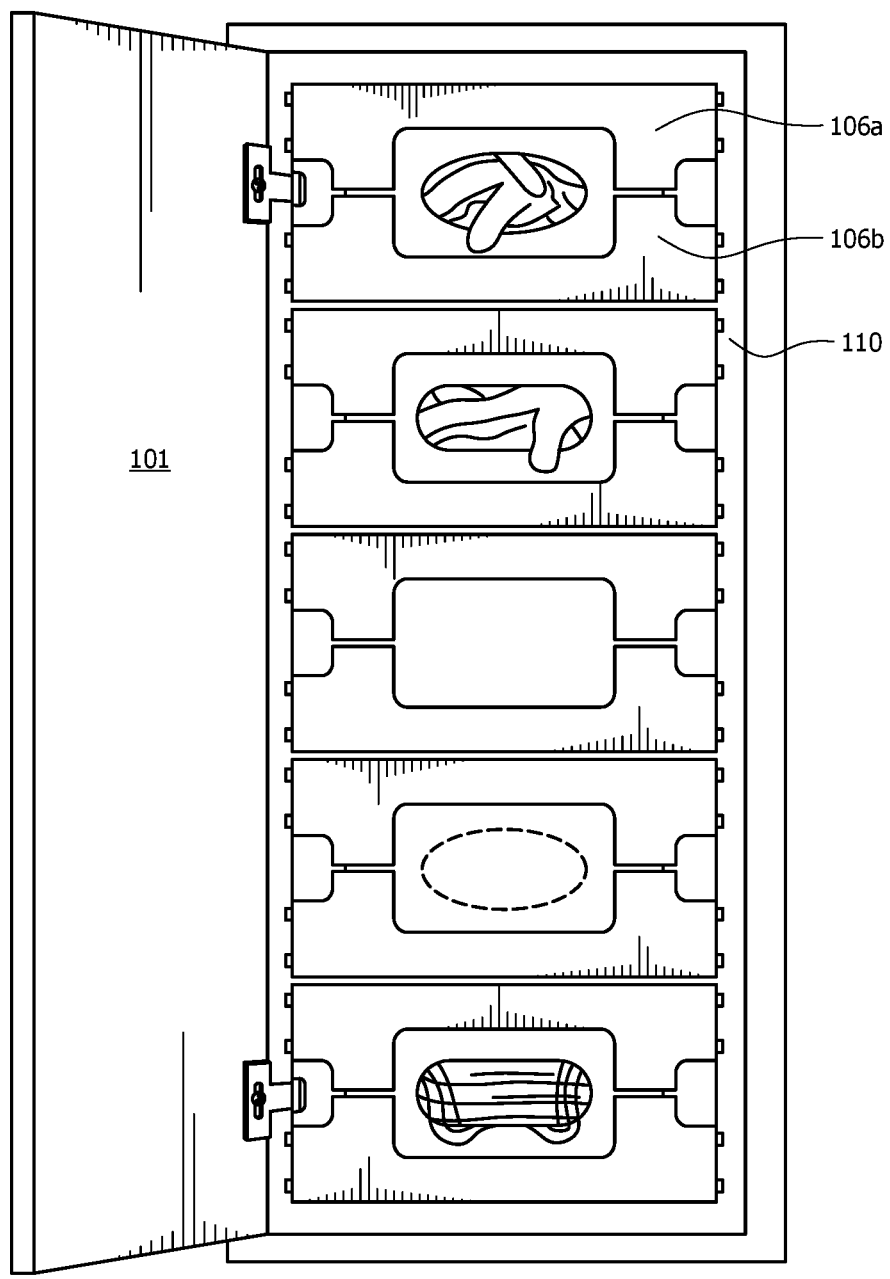
FIG. 6 is a perspective view of a complete cabinet in one embodiment.

FIG. 6 is a perspective view of a complete cabinet in one embodiment. The cabinet in FIG. 6 has a completely different layout and configuration than that of FIG. 1. As noted, in one embodiment this change was completed without any tools. As shown, the cabinet now has two separate gloves boxes with two separate openings as opposed to a single large opening for the apron.

Figure 7:
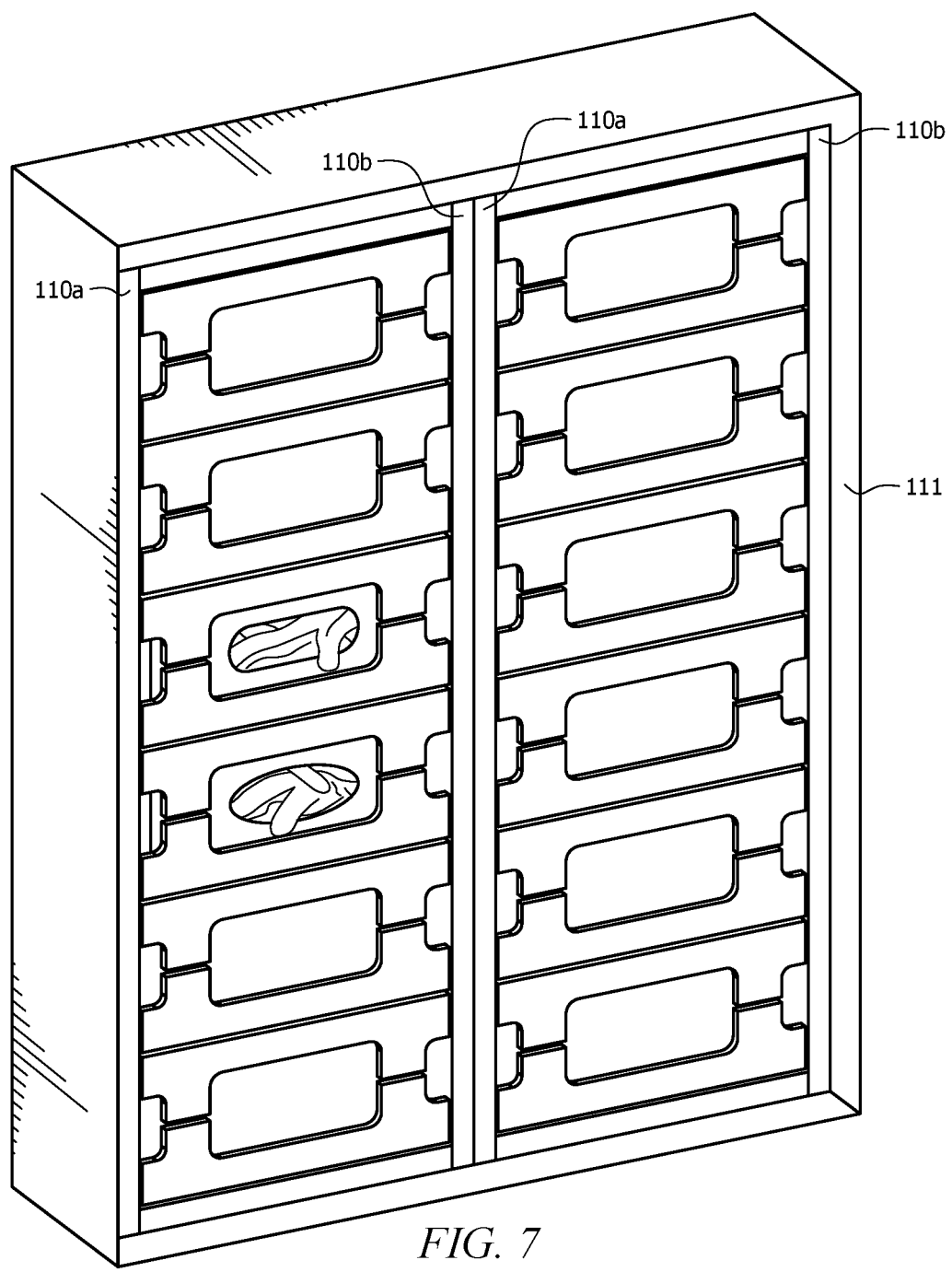
FIG. 7 is an embodiment wherein two rows of covers 106 are joined adjacently in one embodiment.

While one embodiment has been shown where there is only a single column of openings, this is for illustrative purposes only and should not be deemed limiting. As an example, FIG. 7 is an embodiment wherein two columns of covers 106 are joined adjacently in one embodiment. As depicted, the left portion of the cabinet 100 has a left mount 110*a* and a right mount 110*b*. The right portion of the cabinet 100 has a left mount 110*a* and a right mount 110*b*. This allows the first pair of mounts 110 to form a space which allows the covers 106 to mate and couple with the mounts. This creates the first column of openings. Likewise, the second pair of mounts on the rights side of the cabinet 100 form a space allowing the covers 10 to mate and couple with the mounts. This forms a second column of openings. This is yet another opportunity to customize the configuration of the cabinets. Note, while four separate mounts 110 are depicted to create two columns, in other embodiments three mounts 110 can be utilized, with at least one mount 110 having slots 108 on both sides.

Looking at the left column, as shown each opening is uniform. However, in other embodiments, one or more openings can be consolidated into a larger opening to house and display larger contents. There are countless numbers of configurations.

Figure 8:
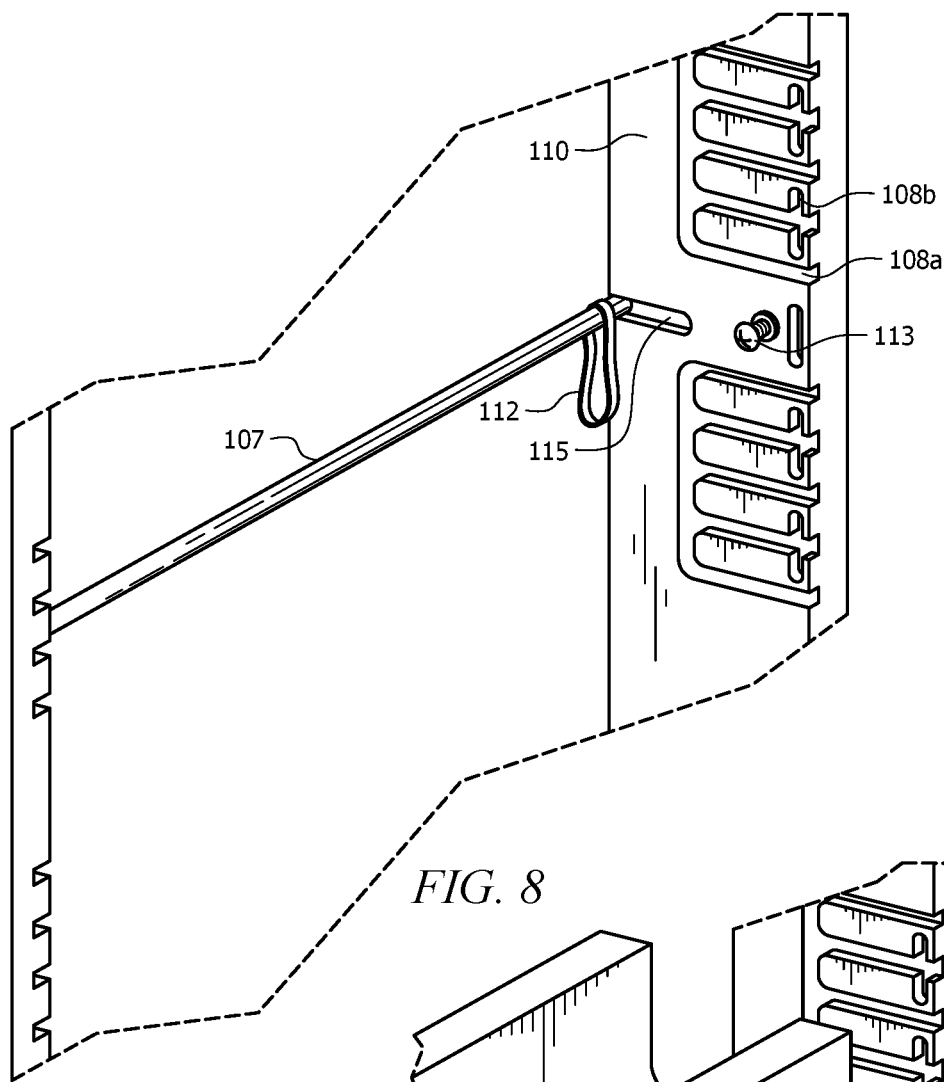
FIG. 8 is a perspective view of the mount in one embodiment.

Turning to FIG. 8, FIG. 8 is a perspective view of the mount in one embodiment. As shown, the mount 110 has a plurality of slots 108 which can couple with the cover 106. As shown, there are a plurality of horizontal slots 108*a* and vertical slots 108*b*. As previously described, in one embodiment the shelves 109 couple with the horizontal slots 108*a*. Thus, anywhere there is a horizontal slot 108*a*, there can be a shelf 109.

Figure 9:
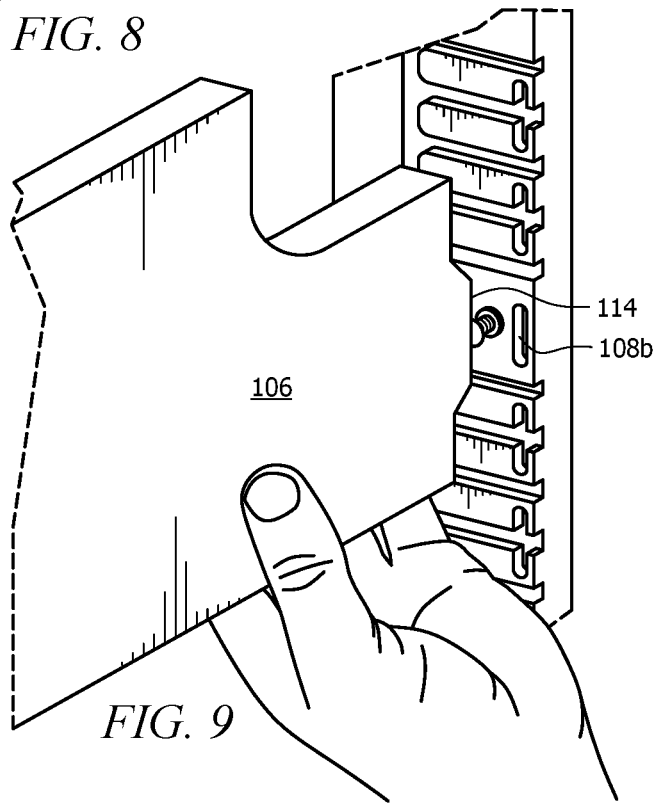
FIG. 9 is a perspective view of the cover with a tab in one embodiment.

In one embodiment the vertical slot 108*b* couples with the tab 114 located on the end of the cover 106. FIG. 9 is a perspective view of the cover 106 with a tab 114 in one embodiment. As can be seen, the tab 114 can be inserted into the vertical slot 108*b*. The same can be repeated on the opposite end (not depicted) of the cover 106. In this fashion, each end of the cover 106 can be coupled with each mount 110. As noted, in one embodiment the cover 106 is coupled and held in place within the vertical slot 108*b* via friction.

In some embodiments the cover 106 has to flex, bend, or compress in order to fit both ends into the vertical slot 108*b*. This provides the counter force which keeps the entire box of gloves, as an example, from being pulled when a user retrieves a pair of gloves.

The vertical slots 108*b* can be discrete slots as depicted in FIG. 9. This means they are of a specified length and are discrete and separate from other slots 108*b*. Discrete slots, in some embodiments, help keep the cover 106 in the desired location because there is no other place for the tab to couple. In other embodiments, however, the vertical slots 108*b* are non-discrete. An elongated vertical slot 108*b* provides many locations along which to couple with the tab, for example.

Also shown in FIG. 8 is the biasing device 112. The biasing device 112, as depicted, couples to the back support 107 and an anchor 113 which remains stationary. The back support 107 can move in the support slot 115. Thus, as shown, the back support 107 can move forward or backwards. In one embodiment the biasing device 112 is a stretchable band which provides a compressive force. This biases the back support 107 toward the anchor 113. This ensures the items are presented in the front-most position.

As noted, in one embodiment the cabinet at least two mounts and at least two covers. In one such embodiment, each of the mounts comprise a plurality of slots, and each cover has at least one tab on each end. To install the covers the tabs of each covers are inserted into the slots to couple the first cover to the mounts. The user determines the appropriate distance for the opening and spaces the second opening as required. In some embodiments a shelf is placed so that the cover can rest upon a shelf. The second cover is then coupled to the mount.

When a user wishes to adjust the cabinet to offer a larger or smaller item, one of the covers is decoupled from the mount. The distance is then adjusted as necessary. A shelf, if needed can be placed so that the item and or the cover can rest upon the shelf. Thereafter, the cover is coupled with the mount.

As noted, while an embodiment has been described with reference to PPE, this is for illustrative purposes and should not be deemed limiting. As an example, in one embodiment the cabinet can be an emergency use cabinet for a school or public building. The emergency use cabinet can house items the user may need in an emergency including a fire extinguisher, a defibrillator, medicines, flares, etc.

Aside from emergency or medical situations, the cabinet can have uses in schools and sports. Large cabinets can house various balls such as footballs, baseballs, etc. Other cabinets can house sport equipment. In still other embodiments the cabinets can house cleaning materials. In other embodiments the cabinet can be used to house various tools or equipment. Virtually any object which is housed and displayed can be used in the system and method discussed herein.

The system and method discussed herein has several benefits. First, because the user can configure the cabinet as desired, there is no longer any need to specifically identify a specific orientation when purchasing. As noted, previously users often had to specify what PPE equipment was going to be housed, and the cabinets were designed and manufactured with that use in mind. Now, however, the user need not specify on the front end.

Second, because the user can configure as desired, the configuration can change from day to date. If a respiratory virus hits, for example, and the user needs more surgical masks and less aprons, the user can change the configuration in a matter of minutes. The cabinet can, in virtually real time, change to reflect the needs of the user. This was not previously possible.

Third, because the device is modular, the space needed for a specific item, gloves as an example, can be increased or decreased. As noted, even the number of columns of openings can be increased or decreased depending upon the desired configuration.

Fourth, in one embodiment the configuration can be altered without tools. Rather than removing nuts, bolts, screws, etc., the covers 106 and shelves 109 utilize friction. This increases the speed in which the configuration can change. As noted, in some embodiments the configuration can be altered in a few minutes.

While the invention has been particularly shown and described with reference to a preferred embodiment, it will be understood by those skilled in the art that various changes in form and detail may be made therein without departing from the spirit and scope of the invention.

What is claimed is:

1. A system for a cabinet, said system comprising:
   said cabinet;
   at least two vertical mounts coupled to said cabinet, wherein said vertical mounts comprise vertical slots and horizontal slots;
   at least two covers, wherein said covers have a first end and a second end, and wherein each end has a tab;
   wherein a tab on the first end releasably couples with a vertical slot on one vertical mount, and wherein the tab on the second end releasably couples with a vertical slot on the other vertical mount;
   wherein said two covers are perpendicular to said vertical mounts.

2. The system of claim 1 wherein said cabinet has a length, and wherein said vertical mounts extend for the length of said cabinet.

3. The system of claim 1 wherein said at least two covers are coupled to said mounts without any tools or screws.

4. The system of claim 1 wherein there is an opening formed between adjacent covers.

5. The system of claim 4 comprising a first item which is retrievable through said opening.

6. The system of claim 1 further comprising a shelf.

7. The system of claim 6 wherein said shelf is approximately perpendicular to said at least two covers.

8. The system of claim 1 comprising four mounts and two columns of covers.

9. The system of claim 1 wherein on of said mounts comprises an anchor and a back support slot.

10. The system of claim 9 further comprising a back support which couples with said back support slot, and wherein a biasing device couples to said anchor to urge the back support.

11. The system of claim 1 wherein said mounts each comprise a plurality of vertically spaced horizontal slots and a plurality of vertically spaced vertical slots.

12. The system of claim 11 wherein said vertically spaced horizontal slots can receive a shelf and wherein said vertically spaced vertical slots can receive a tab located on a mount.

13. The system of claim 12 wherein the distance between adjacent covers can be adjusted to account for larger or smaller items.

14. The system of claim 1 wherein said cabinet comprises a door attached via a hinge.

15. A method for installing a cabinet, wherein said cabinet comprises at least two vertical mounts and at least two covers, wherein each of said mounts comprise a plurality of horizontal and vertical slots, and wherein each cover comprises at least one tab on each end, wherein said method comprises:
- a) coupling a first cover to two of said mounts located on said cabinet via the tab on each end which couples to a vertical slot on each mount;
- b) coupling a second cover to two of said mounts.

16. The method of claim 15 further comprising:
- c) decoupling said second cover from said mounts,
- d) increasing the distance between said first cover and second cover, and,
- e) coupling said second cover to two mounts.

17. The method of claim 15 wherein said cabinet has a length, and wherein said vertical mounts extend for the length of the cabinet.

18. The method of claim 15 further comprising retrieving an item from between said first and second cover.

19. The method of claim 15 further comprising installing a shelf upon which an item can be placed.

* * * * *